(12) United States Patent
Fouquet et al.

(10) Patent No.: US 7,391,512 B2
(45) Date of Patent: Jun. 24, 2008

(54) INTEGRATED OPTOELECTRONIC SYSTEM FOR MEASURING FLUORESCENCE OR LUMINESCENCE EMISSION DECAY

(75) Inventors: Julie E Fouquet, Portola Valley, CA (US); Ian Hardcastle, Sunnyvale, CA (US); Rene P Helbing, Palo Alto, CA (US); Annette C. Grot, Cupertino, CA (US); John Francis Petrilla, Palo Alto, CA (US)

(73) Assignee: Avago Technologies General IP Pte. Ltd., Singapore (SG)

( * ) Notice: Subject to any disclaimer, the term of this patent is extended or adjusted under 35 U.S.C. 154(b) by 286 days.

(21) Appl. No.: 11/017,748

(22) Filed: Dec. 22, 2004

(65) Prior Publication Data
US 2006/0132765 A1    Jun. 22, 2006

(51) Int. Cl.
  *G01N 21/64* (2006.01)
  *G01J 1/58* (2006.01)
  *G01J 3/443* (2006.01)
(52) U.S. Cl. ............... 356/318; 250/458.1; 356/417
(58) Field of Classification Search ................ 356/318, 356/300–334, 417; 250/458.1–461.2
See application file for complete search history.

(56) References Cited

U.S. PATENT DOCUMENTS

| | | | | |
|---|---|---|---|---|
| 3,975,098 A * | 8/1976 | West | ................. | 356/318 |
| 4,037,961 A * | 7/1977 | Macemon | .............. | 356/318 |
| 4,198,567 A * | 4/1980 | Eneroth et al. | ............ | 250/459.1 |
| 4,293,225 A * | 10/1981 | Wheaton et al. | ............ | 356/417 |
| 4,567,370 A * | 1/1986 | Falls | ................. | 250/461.1 |
| 4,626,684 A * | 12/1986 | Landa | ................. | 250/328 |
| 5,323,008 A * | 6/1994 | Studholme et al. | ........ | 250/458.1 |
| 5,548,124 A * | 8/1996 | Takeshima et al. | ........ | 250/458.1 |
| 5,553,616 A * | 9/1996 | Ham et al. | ................. | 600/316 |
| 5,602,446 A * | 2/1997 | Kolber et al. | ............ | 315/241 P |
| 5,666,417 A * | 9/1997 | Liang et al. | ................. | 283/92 |
| 5,721,613 A * | 2/1998 | Linowski et al. | ............ | 356/318 |
| 5,749,830 A * | 5/1998 | Kaneko et al. | .............. | 600/160 |
| 5,990,484 A * | 11/1999 | Ohsuka | ................. | 250/458.1 |
| 5,994,707 A * | 11/1999 | Mendoza et al. | ......... | 250/458.1 |
| 6,121,053 A * | 9/2000 | Kolber et al. | ............ | 436/172 |
| 6,278,521 B1 * | 8/2001 | Jablonski et al. | .......... | 356/402 |
| 6,325,978 B1 * | 12/2001 | Labuda et al. | ................. | 422/84 |

(Continued)

FOREIGN PATENT DOCUMENTS

WO    WO 03/089661    10/2003

OTHER PUBLICATIONS

European Search Report dated May 29, 2006.

*Primary Examiner*—Gregory J. Toatley, Jr.
*Assistant Examiner*—Bryan Giglio
(74) *Attorney, Agent, or Firm*—Bell, Boyd & Lloyd LLP

(57) ABSTRACT

An optoelectronic system for measuring fluorescence or luminescence emission decay, including (a) a light source being a light emitting diode, a semiconductor laser or a flash tube; (b) a first integrated circuit comprising at least one circuit causing the light source to emit light pulses towards a sample which causes a fluorescence or luminescence emission from the sample; (c) a photodiode detecting the emission; (d) a second integrated circuit comprising a detection analysis system determining information about the sample by analyzing decay of the detected emission; and (e) an enclosure enclosing the light source, the first integrated circuit, the second integrated circuit and the photodiode.

21 Claims, 9 Drawing Sheets

U.S. PATENT DOCUMENTS

| | | | |
|---|---|---|---|
| 6,785,447 B2* | 8/2004 | Yoshimura et al. | 385/42 |
| 6,832,729 B1* | 12/2004 | Perry et al. | 235/472.01 |
| 6,836,332 B2* | 12/2004 | Mosley et al. | 356/436 |
| 6,912,050 B2* | 6/2005 | Inberg | 356/317 |
| 6,965,433 B2* | 11/2005 | Zoval et al. | 356/445 |
| 7,198,755 B2* | 4/2007 | Tokhtuev et al. | 422/82.02 |
| 2001/0003044 A1 | 6/2001 | Modlin et al. | |
| 2001/0035501 A1* | 11/2001 | Taylor et al. | 250/461.1 |
| 2002/0113213 A1* | 8/2002 | Amirkhanian et al. | 250/458.1 |
| 2003/0002822 A1* | 1/2003 | Ishihara et al. | 385/88 |
| 2003/0025086 A1* | 2/2003 | Stroka | 250/461.1 |
| 2003/0030012 A1* | 2/2003 | Ahlers et al. | 250/458.1 |
| 2003/0058450 A1* | 3/2003 | Mosley et al. | 356/436 |
| 2003/0080193 A1* | 5/2003 | Ryan et al. | 235/491 |
| 2003/0116436 A1* | 6/2003 | Amirkhanian et al. | 204/452 |
| 2004/0012780 A1 | 1/2004 | Sharma | |
| 2004/0031929 A9* | 2/2004 | Ahlers et al. | 250/458.1 |
| 2004/0089817 A1 | 5/2004 | Long et al. | |
| 2004/0264870 A1* | 12/2004 | Skunes et al. | 385/52 |
| 2005/0013562 A1* | 1/2005 | Tatehata et al. | 385/93 |
| 2005/0088648 A1* | 4/2005 | Grace et al. | 356/318 |
| 2005/0098713 A1* | 5/2005 | Holland | 250/221 |

* cited by examiner

INTEGRATED OPTOELECTRONIC SYSTEM FOR MEASURING FLUORESCENCE OR LUMINESCENCE EMISSION DECAY

BACKGROUND OF THE INVENTION

Optoelectronic systems are used to measure fluorescence or luminescence emission decay in a sample, and to then determine characteristics of the sample from the detected emission. For example, optoelectronic systems measure decay time and amplitude of a detected emission, and then analyze the measured decay time and amplitude to determine materials in, or characteristics of, the sample.

FIG. 1 is a diagram illustrating an example of a conventional optoelectronic system to measure fluorescence or luminescence emission decay. Referring now to FIG. 1, a synchronously pumped, cavity-dumped dye laser system 24 emits light pulses 25 into a sample (not illustrated) on a sample holder 26, to cause a fluorescence or luminescence emission from the sample.

A photomultiplier tube 28 detects the emission. In FIG. 1, photomultiplier tube 28 is shown in its own housing 29. A boxcar integrator module 30 generates an electrical signal from output of photomultiplier tube 28, and a signal processor module 32 processes the electrical signal, to thereby determine information about the sample. A memory module 34 stores a result of integrator module 30, and is accessed by signal processor module 32.

A pickoff beamsplitter 31 splits off a portion of the light emitted by synchronously pumped, cavity-dumped dye laser system 24 and provides the split off portion to a photodiode (PD) 33. The output of photodiode 33 is provided to a variable delay module 36 that produces a variable delay used to gate boxcar integrator module 36.

Typically, synchronously pumped, cavity-dumped dye laser system 24 repeatedly emits light pulses to create multiple identical decays, improving the signal-to-noise ratio.

In this manner, the optoelectronic system determines information about the sample by analyzing, for example, decay time and amplitude of the detected emission.

A display device module 40 can be provided to display the determined information.

As illustrated in FIG. 1, synchronously pumped, cavity-dumped, dye laser system 24 includes, for example, a cavity-dumped dye laser 35, a modelocked pump laser 37, a modelocker electronics module 39 and a cavity dumper electronics module 41.

Various additional components are typically provided. For example, a lens 42 focuses light emitted from synchronously pumped, cavity-dumped dye laser system 24 on the sample, and a lens 44 collects emission from the sample and focuses the collected emission on photomultiplier tube 28. A filter or monochromator 46 is typically provided. If a filter is provided, the filter would be, for example, a wavelength filter which passes the fluorescence or luminescence light from the sample, and blocks wavelengths from laser system 24. Generally, such a filter would typically be a long-wavelength transmitting filter, which blocks short wavelengths and passes longer wavelengths. A monochromator provides a similar function as a filter, by passing only desired wavelengths.

A baffle 48 could be provided to prevent light or other unwanted emission from laser system 24 from overwhelming photomultiplier tube 28.

The specific operation of the various components in FIG. 1 will not be further discussed in detail herein, as such operation is well-known in the art.

FIG. 2 is a diagram illustrating an additional example of a conventional optoelectronic system to measure fluorescence or luminescence emission dynamics. The optoelectronic system in FIG. 2 uses a detection system based on time correlated single photon counting (TCSPC).

Referring now to FIG. 2, a time-to-pulse-height converter module 50, a multi-channel analyzer module 52 and a signal processor module 54 operate together to determine information about the sample from the emission detected by photomultiplier tube 28. A first stage amplifier 56, a second stage amplifier 58, and discriminators 60 and 62 are also provided. TCSCP detection allows fluorescence and luminescence emission dynamics to be followed down to low levels, often $10^{-4}$ of their initial values. This broad dynamic range reveals the non-exponential behavior of luminescence emission from some samples as well as permitting independent measurement of multiple exponential decays. The specific operation of the various components in FIG. 2 will not be further discussed in detail herein, as such operation is well-known in the art.

Unfortunately, the conventional optoelectronic systems in FIGS. 1 and 2 are very large, and can require a fairly large sized room in which to operate.

For example, a typical synchronously pumped, cavity-dumped, dye laser system 24 is a very large system, with many components each typically housed within its own box or enclosure. For example, in FIG. 1, a typical cavity-dumped dye laser 35 and modelocked pump laser 37 each might be, for example, 2 meters long. A typical modelocker electronics module 39 might be, for example 60 centimeters long, 30 centimeters deep and 20 centimeters high. A typical cavity-dumper electronics module 41 might be, for example, 60 centimeters long, 60 centimeters deep and 20 centimeters high.

Further, a typical synchronously pumped, cavity-dumped, dye laser system 24 has high power requirements and is very inefficient.

Moreover, the operation of a synchronously pumped, cavity-dumped, dye laser system 24 requires the use of a vibration isolation table.

In addition, the dye used in cavity-dumped dye laser 35 is toxic and liquid, thereby causing many problems.

In addition, photomultiplier tube 28 would typically be housed in its own housing 29, such as a box or enclosure. Generally, a typical photomultiplier tube 28 in its housing 29 might be, for example, 25 centimeters long, 17 centimeters wide, and 20 centimeters high. A typical photomultiplier tube 28 might be provided with associate drive components (not illustrated) which are, for example, 30 centimeters long, 35 centimeters wide and 10 centimeters high.

The above-described measurements are only general example measurements, and are simply intended to provide a general idea as to the size of various components.

Further, conventionally, boxcar integrator module 30, signal processor module 32, display device module 40, time-to-pulse-height converter module 50, multi-channel analyzer module 52 and signal processor module 54 are provided as separate components, each housed in its own enclosure.

Accordingly, there is a need for a smaller, integrated optoelectronic system in which all the components are enclosed in the same box.

SUMMARY OF THE INVENTION

Various embodiments of the present invention provide an apparatus including (a) a light source being a light emitting diode, a semiconductor laser or a flash tube; (b) an integrated circuit operable to cause the light source to emit light pulses towards a sample which causes a fluorescence or luminescence emission from the sample; (c) a detector detecting the emission; (d) a detection analysis system determining information about the sample by analyzing decay of the detected emission; and (e) an enclosure enclosing the light source, the integrated circuit and the detection analysis system.

Various embodiments of the present invention provide an apparatus including (a) a light source being a light emitting diode, a semiconductor laser or a flash tube; (b) an integrated circuit operable to cause the light source to emit light pluses towards a sample which causes a fluorescence or luminescence emission from the sample; (c) a photodiode detecting the emission; (d) a detection analysis system determining information about the sample by analyzing decay of the detected emission; and (e) an enclosure enclosing the light source, the integrated circuit, the photodiode and the detection analysis system.

Moreover, various embodiments of the present invention provide an apparatus including (a) a light source being a light emitting diode, a semiconductor laser or a flash tube; (b) a first integrated circuit operable to cause the light source to emit light pulses towards a sample which causes a fluorescence or luminescence emission from the sample; (c) a photodiode detecting the emission; (d) a second integrated circuit comprising a detection analysis system determining information about the sample by analyzing decay of the detected emission; and (e) an enclosure enclosing the light source, the first integrated circuit, the second integrated circuit and the photodiode.

Further, various embodiments of the present invention provide an apparatus including (a) a light source emitting light pulses towards a sample which cause a fluorescence or luminescence emission from the sample; (b) a detector detecting the emission; (c) a detection analysis system determining information about the sample by analyzing decay of the detected emission; (d) a first lens directing the light pulses from the light source towards the sample; (e) a second lens directing the emission from the sample towards the detector; and (f) an enclosure enclosing the light source, the detector, the detection analysis system, the first lens and the second lens, wherein the light source, the detector, the first lens and the second lens are properly aligned inside the enclosure.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
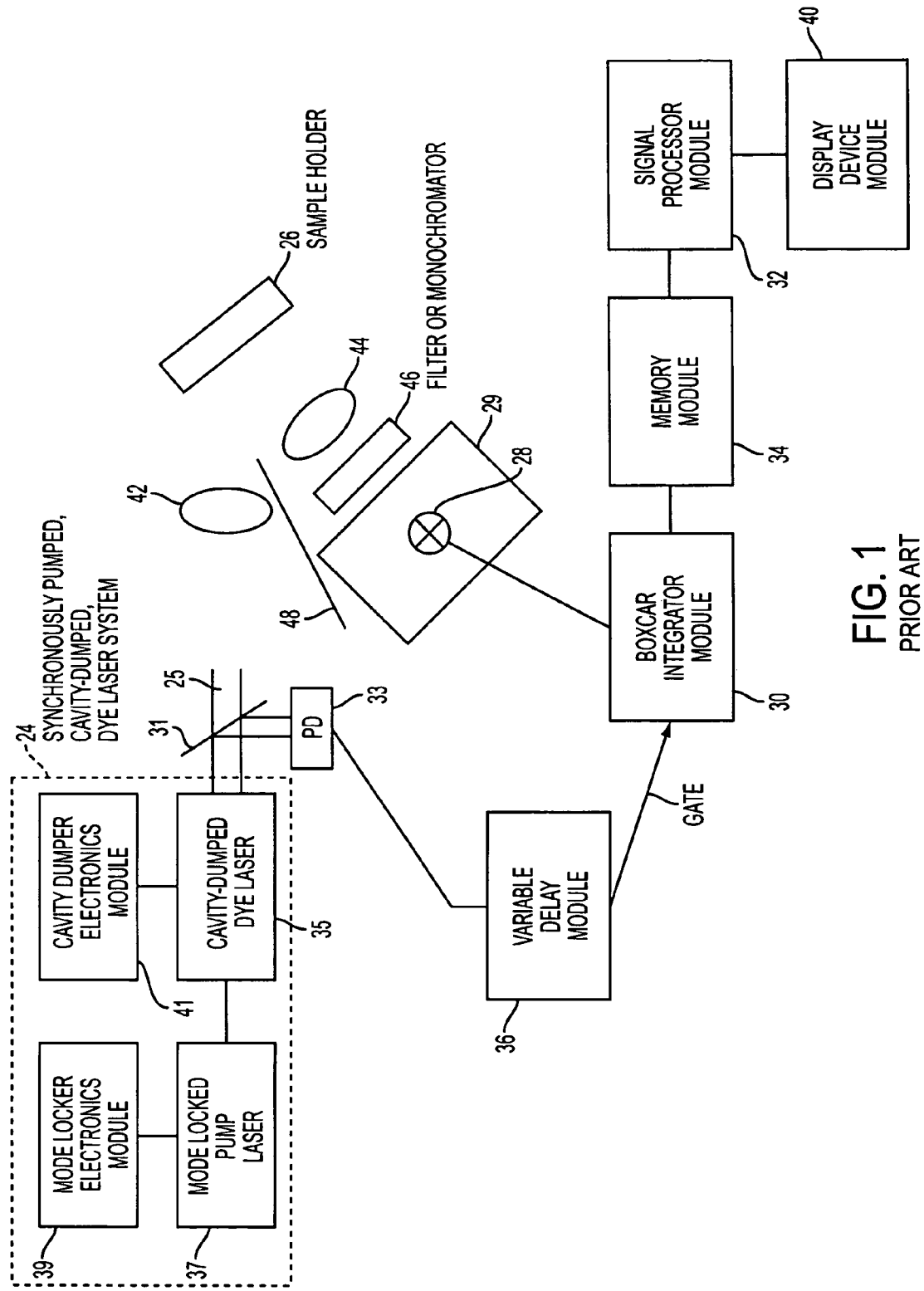
FIG. 1 (prior art) is a diagram illustrating an example of a conventional optoelectronic system to measure fluorescence or luminescence emission decay.
Figure 2:
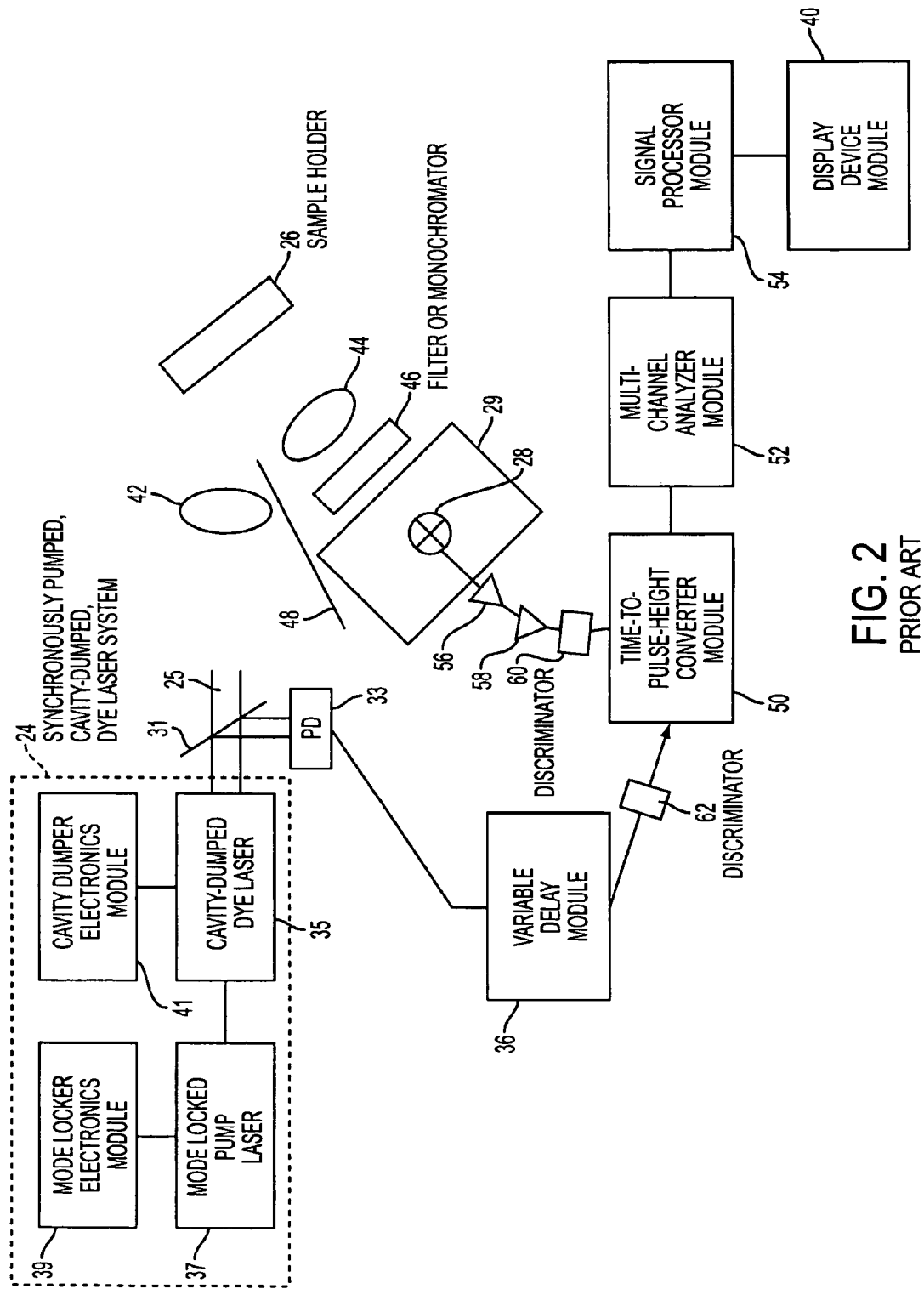
FIG. 2 (prior art) is a diagram illustrating an additional example of a conventional optoelectronic system to measure fluorescence or luminescence emission dynamics.

Reference will now be made in detail to the present preferred embodiments of the present invention, examples of which are illustrated in the accompanying drawings, wherein like reference numerals refer to like elements throughout.

The inventors of the present invention have realized that fluorescence/luminescence measurements do not need sub-picosecond light pulses, but can be made with light pulses of the order of 100 ps. Such measurements therefore do not require the use of a synchronously pumped, cavity-dumped, dye laser system as described above. In various embodiments of the present invention, the light pulses can be generated using, for example, a suitably-structured semiconductor laser, light-emitting diode or a flash tube driven by a suitable driver.

Figure 3:
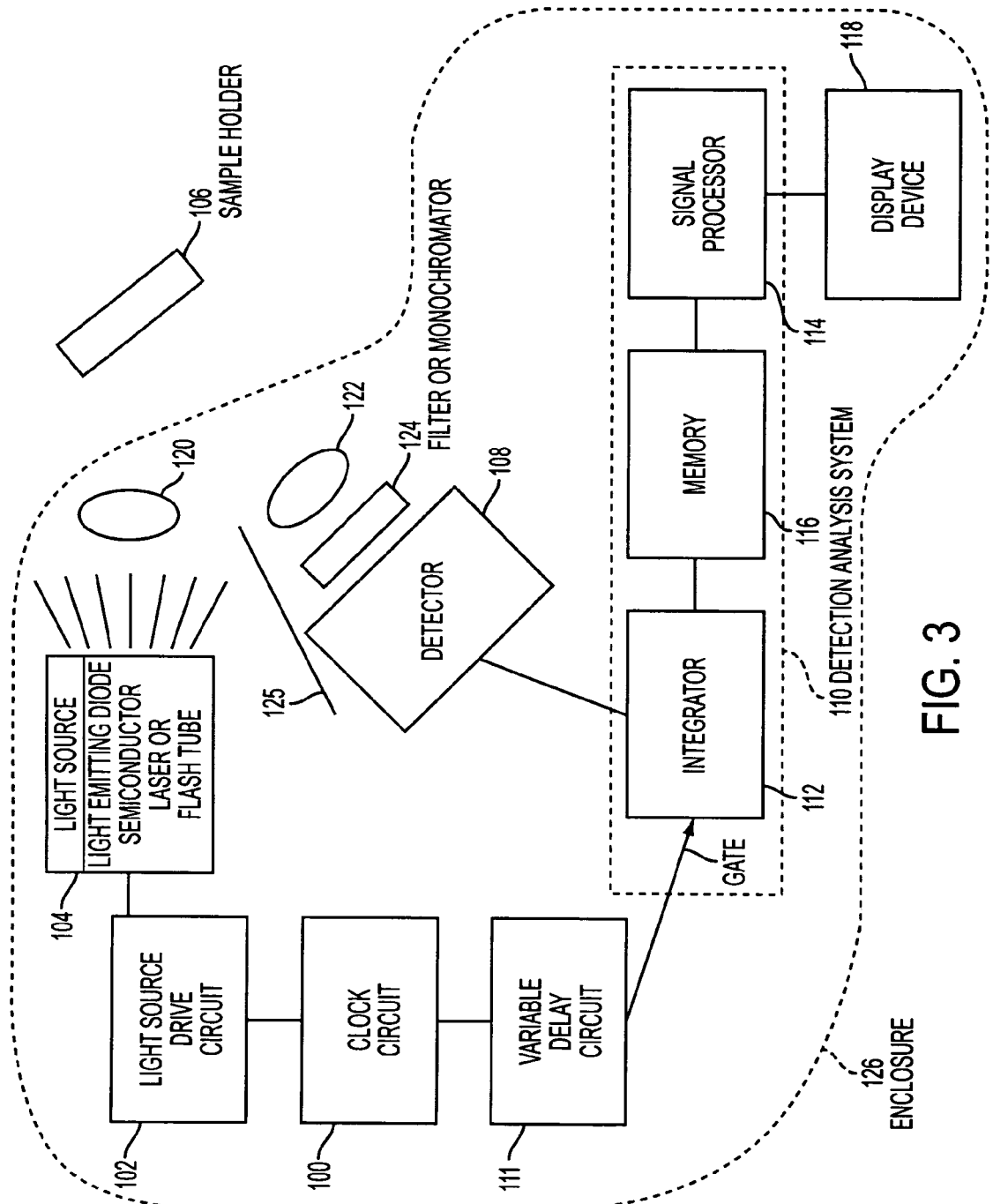
FIG. 3 is a diagram illustrating an optoelectronic system to measure fluorescence or luminescence emission decay, according to an embodiment of the present invention.

FIG. 3 is a diagram illustrating an optoelectronic system to measure fluorescence or luminescence emission decay, according to an embodiment of the present invention. Referring now to FIG. 3, a clock circuit 100 produces a clock signal. A light source drive circuit 102 drives a light source 104 in accordance with the clock signal to emit light pulses towards a sample (not illustrated) on a sample holder 106. In a typical embodiment, light source drive 102 would be, for example, a sub-nanosecond (ns) drive. The clock signal produced by clock circuit 100 would then be an appropriate clock pulse for a sub-ns drive.

Light source 104 is a light emitting device (LED) such as, for example, a light emitting diode or a semiconductor laser or could be a flash tube, which are known devices. Light source drive circuit 102 and clock circuit 100 operate together to cause light source 104 to emit light pulses towards the sample which causes a fluorescence or luminescence emission from the sample. In some embodiments of the present invention, a laser as light source 104 might produce its own clock signal. In such embodiments, a separate clock circuit, such as clock circuit 100, might not be needed.

As indicated above, light source 104 is a light emitting device (LED) such as, for example, a light emitting diode or a semiconductor laser or could be a flash tube. Which specific type of light source to be used would depend, for example, on the wavelength, power and size requirements of the optoelectronic system. Generally, a flash tube has a long pulse, and would typically be suitable for use with materials having longer delay times. A light emitting diode or a semiconductor laser can be made smaller and more power efficient than a flash tube, thereby enabling other associated components in the optoelectronic system to be made smaller.

A detector 108 detects the emission, and generates an electrical signal in response to the detected emission. Detector 108 is, for example, a photodiode, such as an avalanche photodiode or a PIN photodiode. Alternatively, detector 108 could be a photomultiplier tube. Generally, an avalanche photodiode is more sensitive than a PIN photodiode. A photomultiplier tube is generally more sensitive than an avalanche photodiode and much more sensitive than PIN photodiode, but is also much larger and needs a high voltage supply. Avalanche photodiodes, PIN photodiodes and photomultiplier tubes are known devices. However, the present invention is not limited to detector 108 being a photodiode or a photomultiplier tube. Instead, various types of devices, such as, for example, various types of semiconductor sensors, can possibly be used as detector 108.

A detection analysis system 110 determines information about the sample by analyzing the electrical signal generated by detector 108. For example, detection analysis system 110 analyzes decay time and amplitude of the detected emission indicated by the generated electrical signal to determine materials in, or characteristics of, the sample. A variable delay circuit 111 produces a variable delay with respect to the light source drive signal. The variable delay is used by detection analysis system 110 to detect the emission.

In the embodiment in FIG. 3, detection analysis system 110 includes a gated integrator, such as, for example, a boxcar integrator 112, generating an electrical signal, and a signal processor 114 processing the electrical signal, to thereby determine information about the sample. Gated integrators, boxcar integrators and signal processors are known devices.

A memory 116 would typically be provided to store measurements taken by boxcar integrator 112 at different delays, and is accessed by signal processor 114.

A display device 118 displays the information determined by signal processor 114. There are many different types of display devices which could be used as display device 118, and the present invention is not limited to any particular type of display device. As an example, display device 118 might be an LCD. However, display device 118 is not limited to being an LCD.

A lens 120 might be provided to focus light from light source 104 towards the sample, and a lens 122 might be provided to collect emission from the sample and focus the collected emission on detector 108. In some embodiments, lens 120 might even be part of light source 104. A filter or monochromator 124 might also be provided. If a filter is provided, the filter would be, for example, a wavelength filter which passes the fluorescence or luminescence emission from the sample, and blocks wavelengths from light source 104. Generally, such a filter would typically be a long-wavelength transmitting filter, which blocks short wavelengths and passes longer wavelengths. A monochromator provides a similar function. A baffle 125 could be provided to prevent light or other unwanted emission from light source 104 from overwhelming detector 108.

However, the present invention is not limited to the use of lens 120, lens 122, baffle 125 and/or filter or monochromator 124.

In the embodiment in FIG. 3, an enclosure 126, such as a box or other housing structure, encloses light source 104, light source drive circuit 102, clock circuit 100, variable delay circuit 111, detection analysis system 110, display device 118. If detector 108 is a photodiode, enclosure 126 might, for example, also enclose detector 108. If detector 108 is a photomultiplier tube, which is larger than an integrated circuit but is not a huge component, then enclosure 126 may or may not include detector 108, based on design choice. Depending on the specific embodiment, enclosure 126 could include, for example, lens 120, lens 122, baffle 125 and filter or monochromator 124. However, the present invention is not limited to enclosure 126 enclosing all these components, and different components can be enclosed or not enclosed in accordance with system design parameters. However, if the components are enclosed by enclosure 126 as shown in FIG. 3, the optoelectronic system can be a compact, integrated system with all components in one box with proper alignment.

For example, enclosure 126 can be structured to engage with the various components inside enclosure 126 and to define their positions relative to one another, and relative to sample holder 106, so that the system can be used accurately and repeatedly. Such structuring of enclosure 126 can reduce optical alignment and manufacturing costs.

In some embodiments of the present invention, display device 118 would not be inside enclosure 126. Further, in some embodiments of the present invention, a computer interface port, such as a USB port, would be provided instead of display device 118.

Typically, sample holder 106 would not be enclosed by enclosure 126, but would be attachable to/detachable from enclosure 126. However, the present invention is not limited to sample holder 106 being non-enclosed by enclosure 106. Regardless of whether sample holder 106 is enclosed or non-enclosed by enclosure 126, enclosure 126 can be made to accurately position the sample relative to optical elements inside enclosure 126. If sample holder 106 is non-enclosed by enclosure 106, sample holder 106 can be structured to exclude ambient light from entering enclosure 126.

Sample holder 106 is, for example, a slide or a microcuvette, depending on the type of sample or intended use of the optoelectronic system. However, the present invention is not limited to any particular type of sample holder. Typically, sample holder 106 holds a sample at a point where light pulses emitted from light source 104 are focused, and so that emission from the sample can be directed towards detector 108. The positioning of sample holder 106 would, for example, typically be determined by the manufacture of the optoelectronic system.

Figure 4:
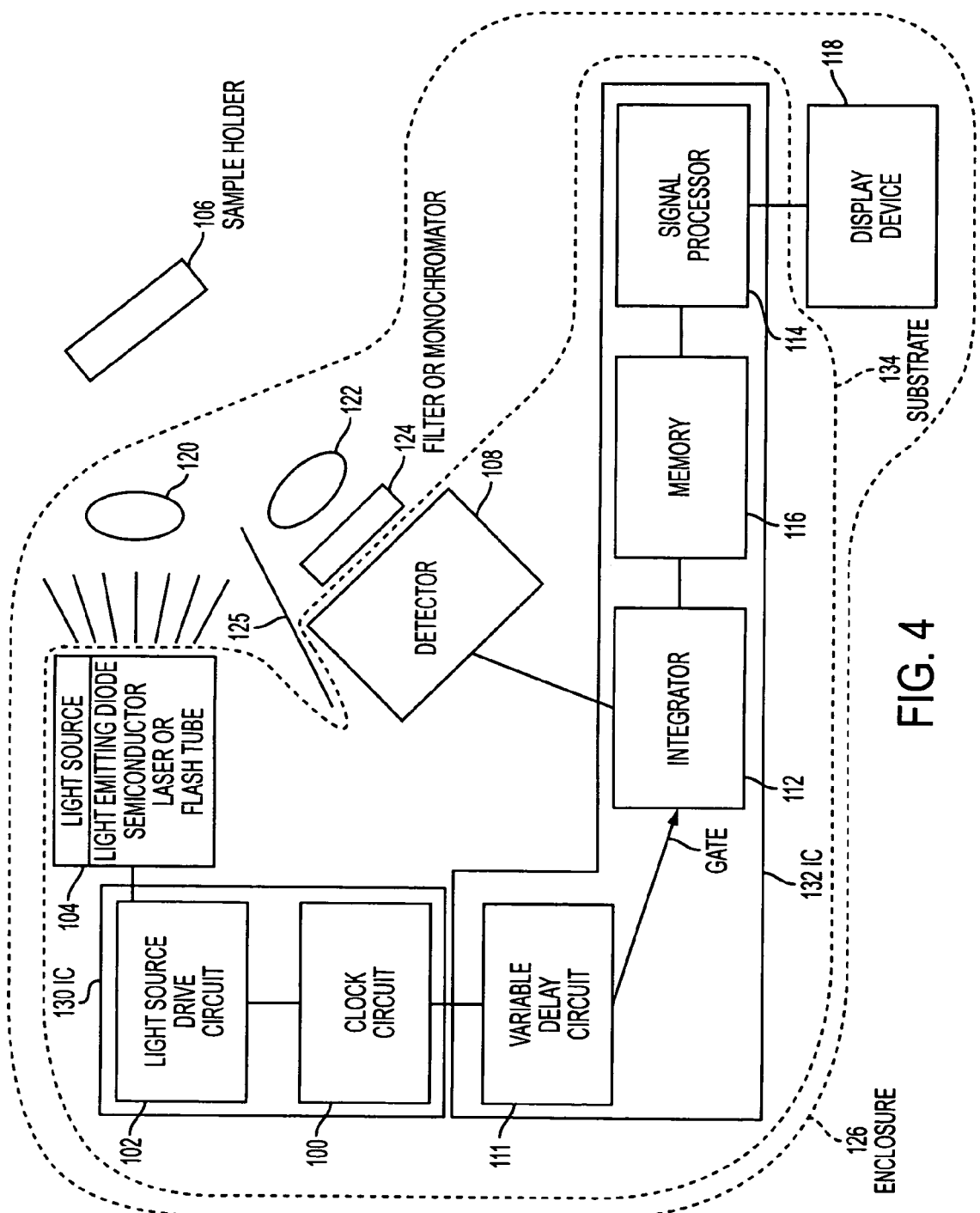
FIG. 4 is a diagram illustrating an optoelectronic system to measure fluorescence or luminescence emission decay, according to an embodiment of the present invention.

FIG. 4 is a diagram illustrating the use of integrated circuits in an optoelectronic system to measure fluorescence or luminescence emission decay, according to an embodiment of the present invention. Referring now to FIG. 4, clock circuit 100 and light source drive circuit 102 are both on the same integrated circuit (IC) 130.

Similarly, variable delay circuit 111, integrator 112, memory 116 and signal processor 114 are on the same integrated circuit 132.

Integrated circuit 130 and 132 are mounted on the same substrate 134. Substrate 134 could be, for example, a printed circuit board (PCB), a flex substrate, a ceramic substrate, or any other suitable substrate.

Light source 104, being a light emitting diode or semiconductor laser, could be on integrated circuit 130 so that light source 104 and associated drive components (such as light source drive circuit 102 and clock circuit 100) are on the same integrated circuit 130. However, including light source 104 on integrated circuit 130 would typically involve too many design compromises. As a result, light source 104 would typically not be included in integrated circuit 130. Instead, light source 104 would typically be mounted near integrated circuit 130 on substrate 134 using, for example, solder ball technology.

Generally, it is often desirable to include source components and circuitry on one integrated circuit, and detection circuitry on a separate integrated circuit. Therefore, source components would typically be on integrated circuit 130, and detection circuitry would typically be on integrated circuit 132. In this manner, there will be fewer design compromises.

In an embodiment of the present invention, baffle 125, filter or monochromator 124, lens 120 and lens 122 may not be on substrate 134, but would be enclosed by enclosure 126.

If a photodiode is used as detector 108, then detector 108 could be provided as a separate integrated circuit on substrate 134. In various embodiments of the present invention, if detector 108 is a suitable type of detector, detector 108 can be on integrated circuit 132.

Display device 118 would typically be provided inside enclosure 126, but would not typically be on substrate 134. If display device 118 is inside enclosure 126, a window (not illustrated) might be provided on enclosure 126 to allow display device to be seen.

Further, instead of using separate integrated circuits 130 and 132, all the components on these integrated circuits could be formed on a single integrated circuit. However, appropriate integrated circuitry design techniques would typically be used to separate source circuitry from detection circuitry to prevent noise from the source circuitry from causing problems with the detection circuitry.

Therefore, various embodiments of the present invention use a light emitting device (LED) such as a light emitting diode or a semiconductor laser or alternatively a flash tube as light source 104, instead of using a synchronously pumped, cavity-dumped, dye laser system as in a conventional optoelectronic system. A light emitting diode, a semiconductor laser or a flash tube has much lower power requirements, has much higher efficiency, and is much smaller than a synchronously pumped, cavity-dumped, dye laser system. As a result, embodiments of the present invention typically do not require the use of a vibration isolation table. In addition, embodiments of the present invention allow for the use of smaller associated circuitry which can be implemented in an integrated circuit. For example, the present invention allows for the associated circuitry to be implemented on integrated circuit 130. Similarly, by using integrated circuit technology, a detection analysis system can be implemented in an integrated circuit. For example, the present invention allows for a detection analysis system to be implemented on integrated circuit 132. By using a light emitting diode, a semiconductor laser or a flash tube, and by implementing integrated circuits, the optoelectronic system can be integrated into a single box, such as enclosure 126.

Moreover, various embodiments of the present invention use a photodiode as detector 108. A photodiode is has much lower power requirements, has much higher efficiency, and is typically smaller than a photomultiplier tube in a conventional optoelectronic system. Therefore, with embodiments of the present invention which use a photodiode as detector 108, detector 108 can easily be integrated into the single box, such as enclosure 126. In addition, some photomultiplier tubes may be small enough to be used as detector 108 and still be enclosed by enclosure 126. Therefore, various embodiments of the present invention provide a much smaller optoelectronic system which is enclosed is a single box, as compared to a conventional optoelectronic system.

Figure 5:
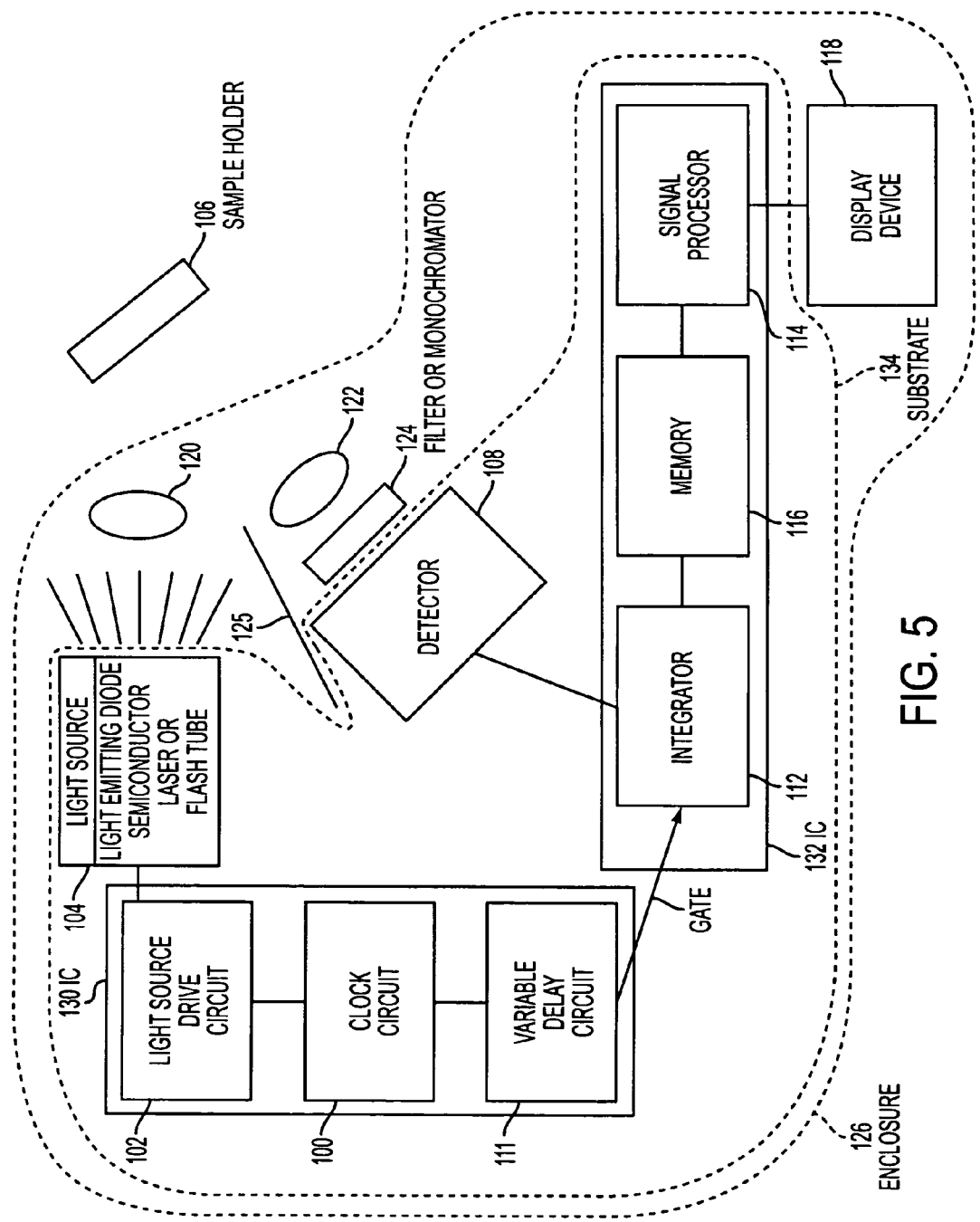
FIG. 5 is a diagram illustrating an optoelectronic system to measure fluorescence or luminescence emission decay, according to an additional embodiment of the present invention.

FIG. 5 is a diagram illustrating an optoelectronic system to measure fluorescence or luminescence emission decay, according to an additional embodiment of the present invention. The embodiment in FIG. 5 is similar to that in FIG. 4, except that variable delay circuit 111 is on integrated circuit 130 instead of on integrated circuit 132. Whether to include variable delay circuit 111 on integrated circuit 130 or integrated circuit 132 is a matter of design choice based on characteristics of the various circuits and integrated circuit technology.

Generally, in a typical embodiment, variable delay circuit 111 would be included on integrated circuit 132 as in FIG. 4, instead of on integrated circuit 130 as in FIG. 5. By including variable delay circuit 111 on integrated circuit 132, the delay circuitry is included on the same integrated circuit as other detection circuitry in detection analysis system 110, which can save on manufacturing and design costs since more sophisticated detection circuitry will require a more sophisticated delay.

Embodiments of the present invention in FIGS. 3-5 disclose detection analysis system 110 comprising an integrator and a signal processor. There are many different possible detection analysis systems which can be used, and many variations of detection analysis systems. Accordingly, embodiments of the present invention are not limited to any particular detection analysis system or any particular variation of a detection analysis system.

Figure 6:
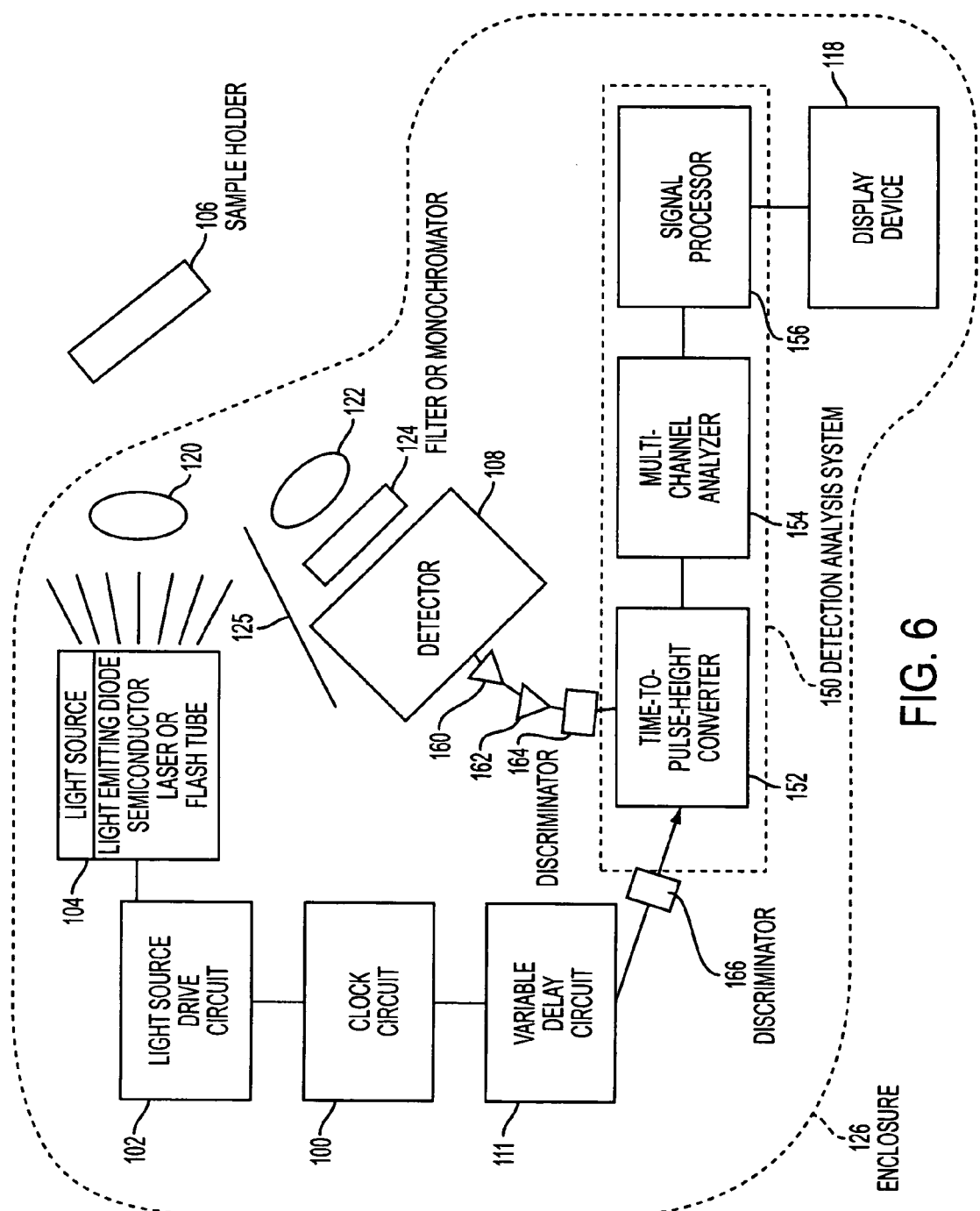
FIG. 6 is a diagram illustrating an optoelectronic system to measure fluorescence or luminescence emission decay, according to a further embodiment of the present invention.

For example, FIG. 6 is a diagram illustrating an optoelectronic system to measure fluorescence or luminescence emission decay, according to an additional embodiment of the present invention. The embodiment of the present invention in FIG. 6 uses a detection analysis system based on time correlated single photon counting (TCSPC). This type of system provides a wide dynamic range so that multiple fluorescence and photoluminescence decays having different amplitudes and different temporal characteristics can be distinguished from each other.

Referring now to FIG. 6, an exemplary embodiment of a detection analysis system 150 includes a time-to-pulse-height converter 152, a multi-channel analyzer 154 and a signal processor 156. Time-to-pulse-height converter 152, multi-channel analyzer 154 and signal processor 156 operate together to determine information about the sample from the emission detected by detector 108.

Detector 108 could be a photodiode. However, in the embodiment of FIG. 6, detector 108 could also be a photomultiplier tube.

In the embodiment in FIG. 6, a first stage amplifier 160, a second stage amplifier 162, and discriminators 162 and 164 might be provided. Generally, first stage amplifier 160 is a preamplifier located adjacent to detector 108 to minimize noise pick-up. Generally, discriminator 164 is a level discriminator that generates a pulse when output of second stage amplifier 162 exceeds a threshold. In an embodiment of the present invention, discriminator 164 is a constant fraction discriminator in which the threshold is a constant percentage of pulse height. However, the present invention is not limited to all of these being provided. For example, in various embodiments, discriminator 166 might not be provided.

In FIG. 6, time-to-pulse-height converter 152 and multi-channel analyzer 154 are shown as separate circuits. However, the functions of these circuits can be combined into a single circuit.

For example, the basic approach is, generally, to measure and classify into statistical bands the delay between reference pulses generated by variable delay circuit 111 and pulses generated by discriminator 164. Instead of using a separate time-to-pulse height converter 152 and multi-channel analyzer 154, digital circuitry can be implemented to gate a clock signal ON with each reference pulse and gate it OFF with the discriminator pulse and count the clock cycles.

Detection analysis system 150 can be embodied in a single integrated circuit, such as a single digital signal processor (DSP) chip which is suitable programmed.

Figure 7:
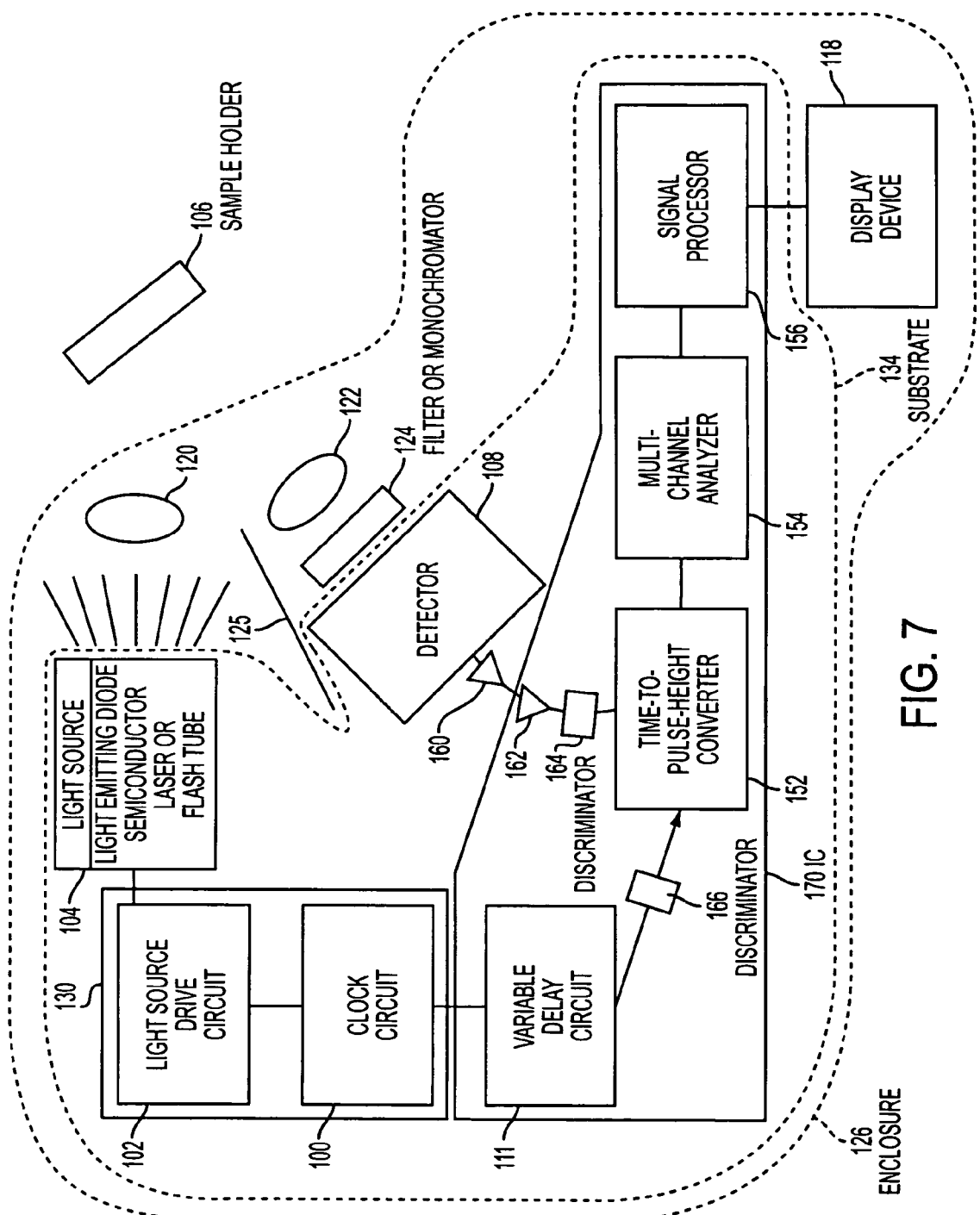
FIG. 7 is a diagram illustrating an optoelectronic system to measure fluorescence or luminescence emission decay, according to an additional embodiment of the present invention.

FIG. 7 is a diagram illustrating the use of integrated circuits in an optoelectronic system to measure fluorescence or luminescence emission decay, according to an additional embodiment of the present invention. Referring now to FIG. 7, clock circuit 100 and light source drive circuit 102 are both on the same integrated circuit 130.

Similarly, time-to-pulse-height converter 152, multi-channel analyzer 154 and signal processor 156 are on the same integrated circuit (IC) 170.

Moreover, in an embodiment of the present invention, second stage amplifier 162 and discriminator 164 are on IC 170. If discriminator 166 is provided, then discriminator 166 could also be provided on integrated circuit 170. In a typical embodiment, first stage amplifier 160 would not be provided on integrated circuit 170 in order to reduce pickup of interference. Which components to be included on integrated circuit 130 and/or integrated circuit 170 is a matter of design choice based on characteristics of the various circuits and integrated circuit technology. Therefore, the present invention is not limited to any particular components being included on a particular integrated circuit.

Integrated circuit 130 and 170 would typically be mounted on the same substrate 134.

In FIG. 7, time-to-pulse-height converter 152 and multi-channel analyzer 154 are shown as separate circuits. However, the functions of these circuits can be combined into a single circuit provided on integrated circuit 170.

Further, instead of using separate integrated circuits 130 and 170, all the components on these integrated circuits could be formed on a single integrated circuit.

Figure 8:
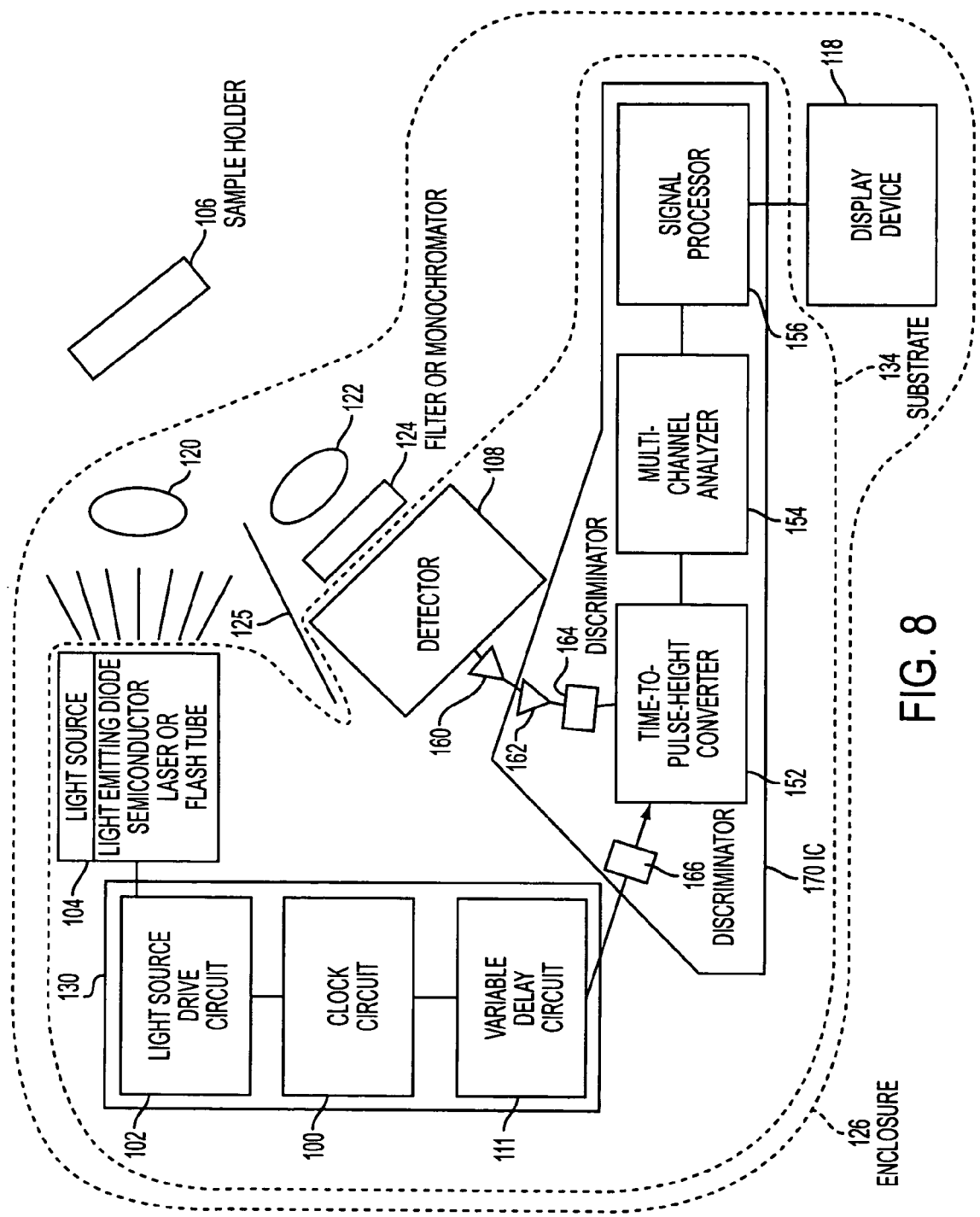
FIG. 8 is a diagram illustrating an optoelectronic system to measure fluorescence or luminescence emission decay, according to an additional embodiment of the present invention.

FIG. 8 is a diagram illustrating an optoelectronic system to measure fluorescence or luminescence emission decay, according to an additional embodiment of the present invention. The embodiment in FIG. 8 is similar to that in FIG. 7, except that variable delay circuit 111 is on integrated circuit 130 instead of on integrated circuit 170. Whether to include variable delay circuit 111 on integrated circuit 130 or integrated circuit 170 is a matter of design choice based on characteristics of the various circuits and integrated circuit technology.

In the above figures, sample holder 106 is shown as being non-enclosed by enclosure 126. However, as described above, in embodiments of the present invention, sample holder 106 can be enclosed by enclosure 126.

Figure 9:
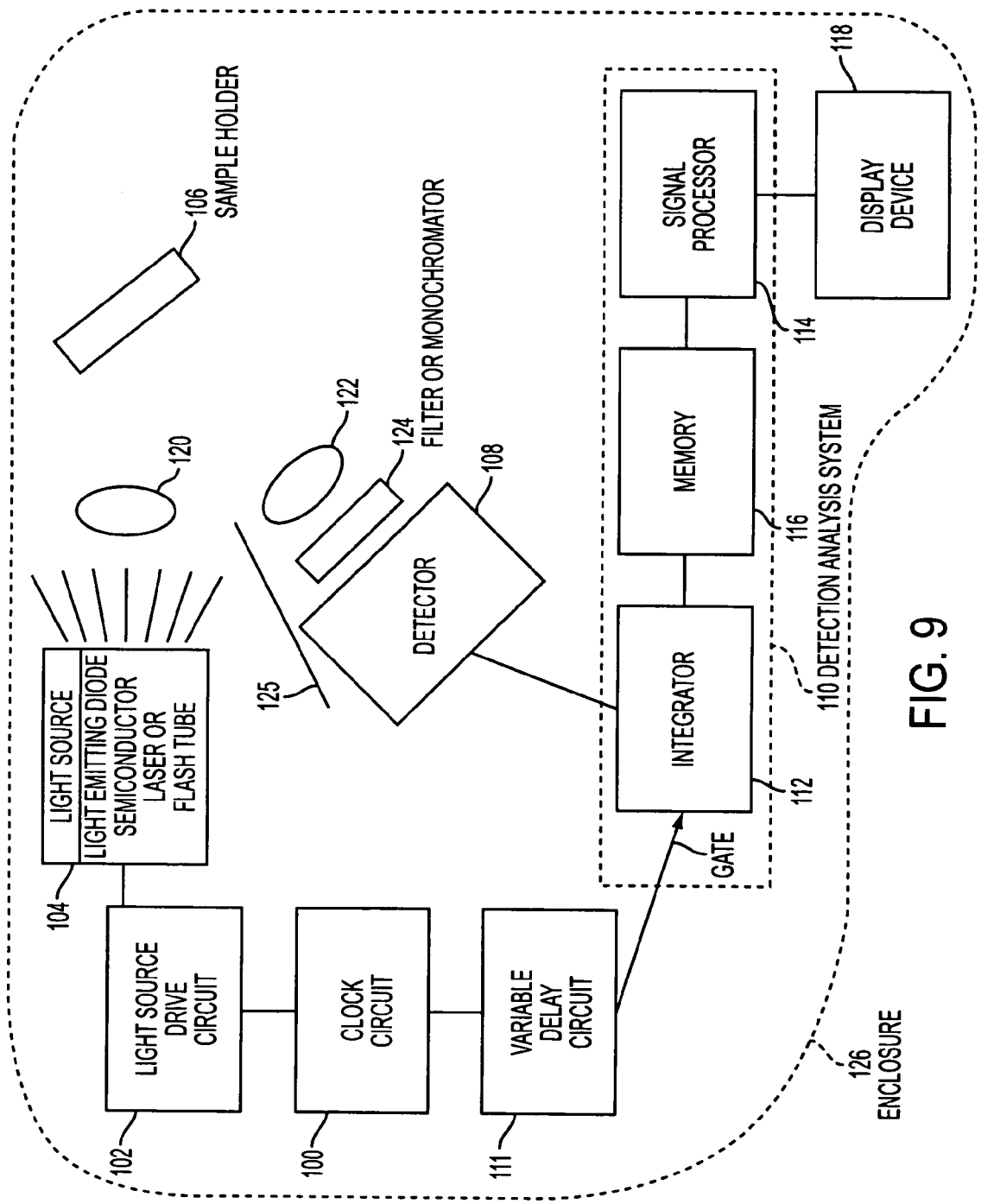
FIG. 9 is a diagram illustrating an optoelectronic system to measure fluorescence or luminescence emission decay, according to an additional embodiment of the present invention.

For example, FIG. 9 is a diagram illustrating an optoelectronic system which is similar to that in FIG. 3, except that sample holder 106 is shown as being enclosed by enclosure 126.

As would be understood from the above, generally, according to embodiments of the present invention, decay properties of a sample are measured, and the measured decay properties are analyzed.

Various embodiments of the present invention include the use of lenses, such as lenses 120 and 122. Such lenses would typically be enclosed by enclosure 126 so that the lenses and other components inside enclosure 126 can be aligned by the manufacturer with respect to each other, and with respect to the sample.

Various embodiments of the present invention relate to the formation of various components on an integrated circuit. Typically, the formation of various components on an integrated circuit, as described herein, would be based on, for example, silicon CMOS technology. Silicon Germanium (SiGe) heterojunction bipolar transistor technology could also be used to form components on an integrated circuit. However, the present invention is not limited to any particular technology for the formation of components on an integrated circuit.

Various embodiments of the present invention relate to the inclusion of specific components on an integrated circuit. However, which components to include on a specific integrated circuit and which components to exclude from the integrated circuit, is within design choice. Therefore, the present invention is not limited to any specific components being included on any specific integrated circuit, or any specific number of integrated circuits.

Various embodiments of the present invention relate to the inclusion of specific components on a substrate. However, which components to include on a substrate and which components to exclude from the substrate, is within design choice. Therefore, the present invention is not limited to any specific components being included on, or excluded from, a substrate.

In various embodiments of the present invention, a detected fluorescence or luminescence emission is detected and analyzed. For example, the decay time and amplitude of the detected emission might be analyzed. However, embodiments of the present invention are not limited to any particular characteristic of a detected emission being analyzed.

The various figures disclose emitted light pulses and various optical components. It should be understood that the emitted light pulses and the various optical components should be properly aligned, although such alignment may not be accurately shown in the figures.

Various embodiments of the present invention include an enclosure, such as enclosure 126, to house various components. The use of an enclosure in various embodiments of the present invention allows, for example, the housed components to be properly aligned together and with respect to a sample. Moreover, the use of an enclosure in various embodiments of the present invention allows, for example, the system to be sold and transported as a unit, and to be located in a room as a unit.

Although a few preferred embodiments of the present invention have been shown and described, it would be appreciated by those skilled in the art that changes may be made in these embodiments without departing from the principles of the invention, the scope of which is defined in the claims and their equivalents.

What is claimed is:

1. An apparatus comprising:
   a light source being a light emitting diode, a semiconductor laser or a flash tube;
   an integrated circuit operable to cause the light source to emit light pulses;
   a first lens directing the light pulses from the light source towards a sample, which causes a fluorescence or luminescence emission from the sample, the first lens being positioned between the light source and the sample such that the first lens is adjacent to the sample;
   a detector detecting the emission;
   a second lens directing the emission from the sample towards the detector, the second lens being positioned between the sample and the detector such that the second lens is adjacent to the sample;
   a detection analysis system determining information about the sample by analyzing decay of the detected emission; and
   an enclosure enclosing the light source, the integrated circuit, the first lens, the detector, the second lens, and the detection analysis system.

2. An apparatus as in claim 1, further comprising:
a substrate on which the integrated circuit and the detection analysis system are mounted.

3. An apparatus as in claim 1, further comprising:
a substrate on which the integrated circuit, the light source and the detection analysis system are mounted.

4. An apparatus as in claim 1, wherein the integrated circuit comprises:
a clock circuit producing a clock signal; and
a light source drive circuit driving the light source in accordance with the clock signal to emit the light pulses towards the sample.

5. An apparatus as in claim 1, wherein the integrated circuit comprises:
a clock circuit producing a clock signal;
a light source drive circuit driving the light source in accordance with the clock signal to emit the light pulses towards the sample; and
a variable delay circuit producing a variable delay used by the detection analysis system to detect the emission.

6. An apparatus as in claim 1, wherein the detection analysis system comprises:
a detection analysis system integrated circuit comprising a gated integrator generating an electrical signal; and
a signal processor processing the electrical signal, to thereby determine the information about the sample.

7. An apparatus as in claim 6, wherein the signal processor is on the detection analysis system integrated circuit.

8. An apparatus as in claim 6, wherein the detector is a photodiode.

9. An apparatus as in claim 1, wherein the detector is a photodiode.

10. An apparatus as in claim 6, further comprising:
a substrate on which the integrated circuit and the detection analysis system integrated circuit are mounted.

11. An apparatus as in claim 1, wherein the detection analysis system comprises:
a detection analysis system integrated circuit comprising a time-to-pulse-height converter;
a multi-channel analyzer; and
a signal processor, wherein the time-to-pulse-height converter, the multi-channel analyzer and the signal processor operate together to determine the information about the sample from the detected emission.

12. An apparatus as in claim 11 wherein the multi-channel analyzer is on the detection analysis system integrated circuit.

13. An apparatus as in claim 11, wherein the multi-channel analyzer and the signal processor are on the detection analysis system integrated circuit.

14. An apparatus as in claim 2, further comprising:
a display device displaying the information, wherein the display device is on the substrate and enclosed by the enclosure.

15. The apparatus of claim 1, further comprising a monochromator between the second lens and the detector.

16. An apparatus comprising:
a light source being a light emitting diode, a semiconductor laser or a flash tube;
an integrated circuit operable to cause the light source to emit light pluses;
a first lens directing the light pulses from the light source towards a sample, which causes a fluorescence or luminescence emission from the sample, the first lens being positioned between the light source and the sample such that the first lens is adjacent to the light source and the sample;
a photodiode detecting the emission;
a second lens directing the emission from the sample towards the photodiode, the second lens being positioned between the sample and the photodiode such that the second lens is adjacent to the sample and the photodiode;
a detection analysis system determining information about the sample by analyzing decay of the detected emission; and
an enclosure enclosing the light source; the integrated circuit, the first lens, the photodiode, the second lens, and the detection analysis system.

17. An apparatus as in claim 16, further comprising:
a substrate on which the integrated circuit and the detection analysis system are mounted.

18. An apparatus as in claim 16, further comprising:
a substrate on which the integrated circuit, the light source and the detection analysis system are mounted.

19. An apparatus as in claim 16, wherein the integrated circuit comprises:
a clock circuit producing a clock signal; and
a light source drive circuit driving the light source in accordance with the clock signal to emit the light pulses towards the sample.

20. An apparatus as in claim 16, wherein the integrated circuit comprises:
a clock circuit producing a clock signal;
a light source drive circuit driving the light source in accordance with the clock signal to emit the light pulses towards the sample; and
a variable delay circuit producing a variable delay used by the detection analysis system to detect the emission.

21. An apparatus comprising:
a light source being a light emitting diode, a semiconductor laser or a flash tube;
a first integrated circuit operable to cause the light source to emit light pulses;
a first lens directing the light pulses from the light source towards a sample, which causes a fluorescence or luminescence emission from the sample, the first lens being positioned between the light source and the sample such that the first lens is adjacent to the light source and the sample;
a photodiode detecting the emission;
a second lens directing the emission from the sample towards the photodiode, the second lens being positioned between the sample and the photodiode such that the second lens is adjacent to the sample and the photodiode;
a second integrated circuit comprising a detection analysis system determining information about the sample by analyzing decay of the detected emission; and
an enclosure enclosing the light source, the first integrated circuit, the first lens, the photodiode, the second lens, and the second integrated circuit.

* * * * *